(12) United States Patent
Rebec et al.

(10) Patent No.: US 11,484,227 B2
(45) Date of Patent: Nov. 1, 2022

(54) METHOD FOR CONDITIONING OF A SENSOR

(71) Applicant: WaveForm Technologies, Inc., Salem, NH (US)

(72) Inventors: Mihailo V. Rebec, Portland, OR (US); Robert Bruce, Beaverton, OR (US); Ralph Dutt-Ballerstadt, Portland, OR (US)

(73) Assignee: WAVEFORM TECHNOLOGIES, INC., Salem, NH (US)

( * ) Notice: Subject to any disclaimer, the term of this patent is extended or adjusted under 35 U.S.C. 154(b) by 377 days.

(21) Appl. No.: 16/178,431

(22) Filed: Nov. 1, 2018

(65) Prior Publication Data

US 2019/0125225 A1    May 2, 2019

Related U.S. Application Data (60) Provisional application No. 62/580,376, filed on Nov. 1, 2017.

(51) Int. Cl.
*A61B 5/145* (2006.01)
*A61B 5/1495* (2006.01)
(Continued)

(52) U.S. Cl.
CPC ........ *A61B 5/14532* (2013.01); *A61B 5/1486* (2013.01); *A61B 5/1495* (2013.01); *G01N 27/49* (2013.01)

(58) Field of Classification Search
CPC ............ A61B 5/14532; A61B 5/14865; A61B 5/1486; A61B 5/1495; A61B 5/1473;
(Continued)

(56) References Cited

U.S. PATENT DOCUMENTS

| | | | | |
|---|---|---|---|---|
| 5,800,420 A | * | 9/1998 | Gross | .................. A61K 9/7023 604/890.1 |
| 2005/0161346 A1 | * | 7/2005 | Simpson | .............. A61B 5/1486 205/792 |

(Continued)

FOREIGN PATENT DOCUMENTS

EP         2228642 A1    9/2010
WO    2017/021534 A1    2/2017

OTHER PUBLICATIONS

Patent Cooperation Treaty: International Search Report and Written Opinion for PCT/US2018/058775 dated Mar. 5, 2019; 30 pages.

*Primary Examiner* — Sean P Dougherty
*Assistant Examiner* — Kyle W. Kretzer
(74) *Attorney, Agent, or Firm* — Schwabe, Williamson & Wyatt, PC (57) ABSTRACT

A method of in vivo conditioning of an indwelling sensor to reduce run-in time, (stabilization time) comprising: a) applying a first potential to the sensor and measuring a first current at the first potential; b) applying a second potential to the sensor and measuring a second current at the second potential; c) determining a relationship of the first current measured to the second current measured; repeating a, b, and c until the relationship between the first current measured and the second current measured has stabilized, thereby reducing sensor run-in time.

21 Claims, 12 Drawing Sheets

(51) Int. Cl.
 *A61B 5/1486* (2006.01)
 *G01N 27/49* (2006.01)
(58) Field of Classification Search
 CPC ........ A61B 2560/0223; A61B 5/14503; A61B 5/1451; A61B 5/7221; A61B 5/7246; A61M 2230/201; G01N 27/3274
 See application file for complete search history.

(56) References Cited

U.S. PATENT DOCUMENTS

| | | | |
|---|---|---|---|
| 2007/0173712 A1* | 7/2007 | Shah | G01N 27/3274 73/1.01 |
| 2012/0108931 A1 | 5/2012 | Taub | |
| 2012/0262298 A1 | 10/2012 | Bohm | |
| 2012/0265037 A1* | 10/2012 | Bohm | A61B 5/7267 600/309 |
| 2015/0008143 A1 | 1/2015 | Lin et al. | |
| 2017/0038331 A1* | 2/2017 | Macfie | G01N 27/3274 |
| 2019/0000358 A1* | 1/2019 | Patel | A61B 5/14532 |

\* cited by examiner

METHOD FOR CONDITIONING OF A SENSOR

CROSS-REFERENCE TO RELATED APPLICATION

This application claims the priority benefit of the earlier filing date of U.S. Provisional Application No. 62/580,376, filed Nov. 1, 2017, which is specifically incorporated herein by reference in its entirety.

TECHNICAL FIELD

Embodiments herein relate to the field of sensors, and, more specifically, to the conditioning of a sensor to obtain consistent readings and reduce background artifacts.

BACKGROUND

Continuous sensors, such as continuous glucose monitoring (CGM) sensors, are used to measure data continuously, e.g., in a continuous data stream and/or sampled data points over a time interval. Typically, the data is inconsistent for a period of time as the sensor acclimates to the in vivo conditions. Currently all CGM systems require a so-called run-in time, and immediately after insertion of the sensor the measurement is not reliable. This, it would be advantageous if this time (which might differ from insertion site to insertion site) could be reduced.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF THE DISCLOSURE

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope is defined by the appended claims and their equivalents.

Various operations may be described as multiple discrete operations in turn, in a manner that may be helpful in understanding the disclosure; however, the order of description should not be construed to imply that these operations are order dependent.

The description may use perspective-based descriptions such as up/down, back/front, and top/bottom. Such descriptions are merely used to facilitate the discussion and are not intended to restrict the scope of the disclosure.

The terms "coupled" and "connected," along with their derivatives, may be used. It should be understood that these terms are not intended as synonyms for each other. Rather, in particular aspects, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Continuous glucose monitoring technology has been used in the management of diabetes for many years now. Traditional devices use enzymatic methods to measure glucose concentration and provide sample information. In future applications the continuous glucose sensor may become a critical component of the closed loop insulin delivery system and, as such, must be selective, rapid, predictable and acceptable for continuous patient use.

One of the problems facing the implementation of such systems is the time it takes for a glucose sensor to stabilize after it has been inserted. This "run-in" time can last hours, making it difficult to assess the accuracy of the initial measurements. This is especially important in an emergent blood glucose crisis, where accurate measurement is critical for glucose and/or insulin management. To address the issue of long run-in times, the inventors have developed methods of preconditioning the sensors, for example in vivo after insertion or in vitro, and to specifically determine the completion of the run-in process for a sensor. The rapid identification of the completion of the run in (stabilization) can be determined and could provide a means of starting sooner based on an assessment on how much of the stabilization was complete.

Figure 1:
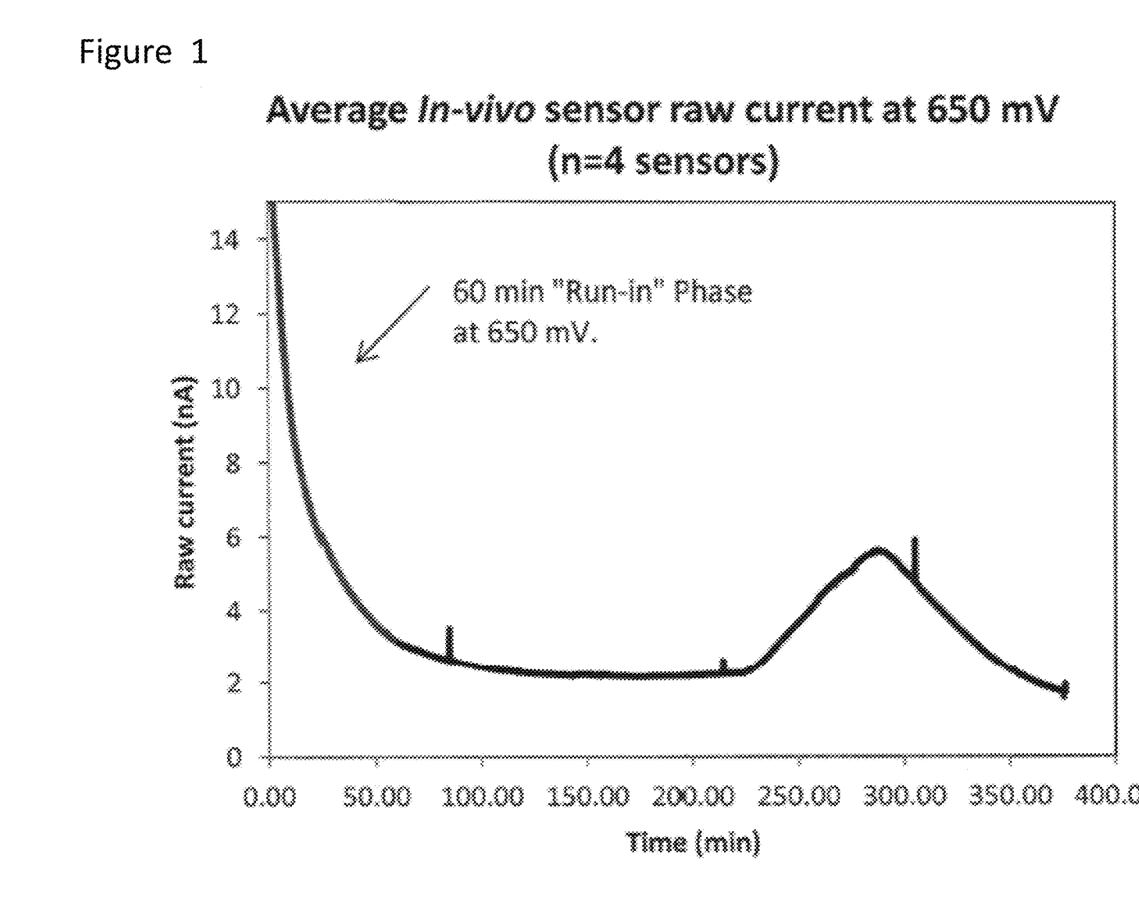
FIG. 1 is a graph showing the average current from four sensors with an applied potential of 650 mV, in accordance with various aspects described herein.
Figure 2:
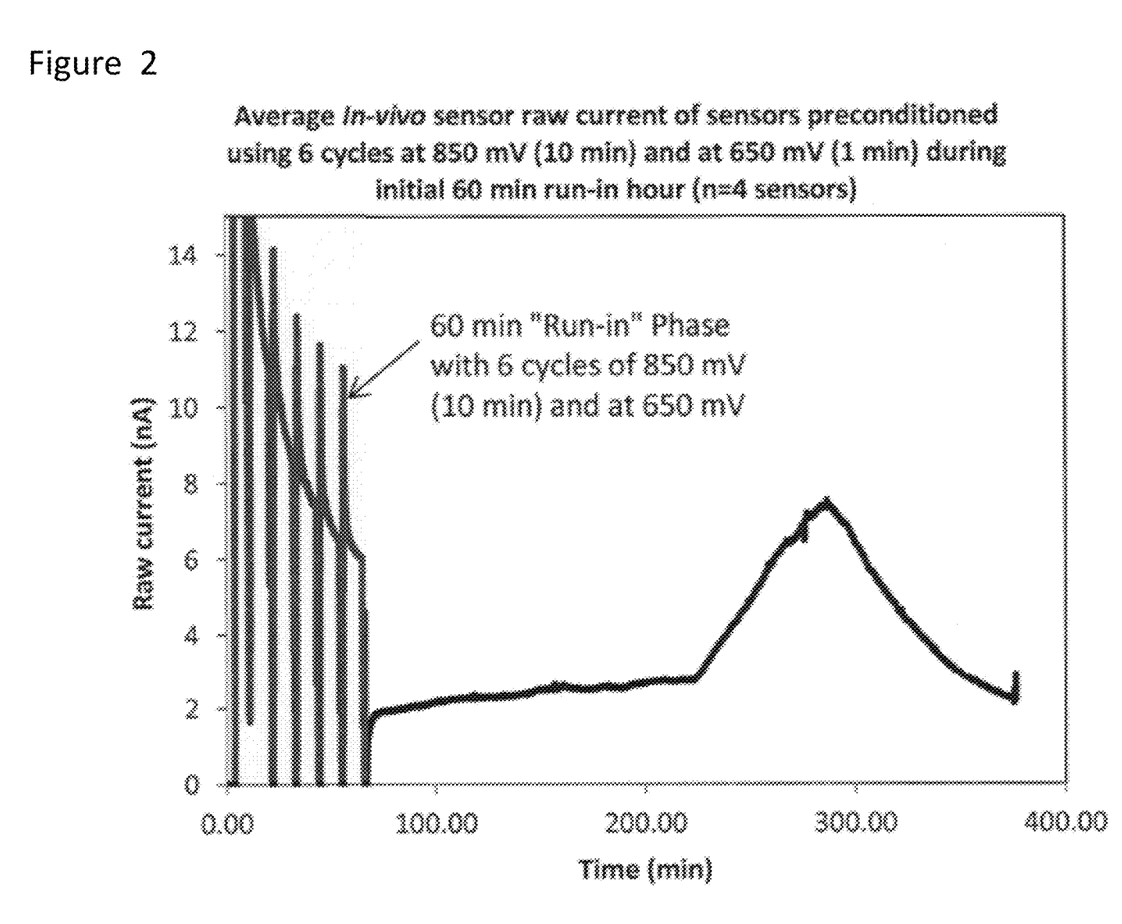
FIG. 2 is a graph showing the average current from four sensors that were preconditioned with several cycles of applied potentials of 850 mV and 650 mV, in accordance with various aspects described herein.

The disclosed methods reduce this run-in time, in certain embodiments to sub-hour times. In addition, as shown in FIGS. 1 and 2, this precondition also results in a sensor that is not as susceptible to current drift even after the run-in period. For example, as shown in FIG. 1 even after the sensor has proceeded through the run-in time, when a potential of 650 mV is applied the base line current drifts slowly downward as a function of time. This baseline drift can lead to erroneous glucose readings and/or the need to continually calibrate the sensor to measured blood glucose levels. In contrast, as shown in FIG. 2, sensors subjected to the disclosed preconditioning method do not show such a drift (see also FIGS. 11 and 12, which show a reduction in spurious signals for a preconditioned sensor, FIG. 11, vs. non-preconditioned sensors, FIG. 12). Furthermore, one of the remarkable results was that the disclosed methods result in sensors that more accurately reflect the actually blood glucose values (see, for example, FIGS. 4, 5, 8, and 9).

Various aspects of a method of conditioning of a sensor such as in vivo conditioning a sensor, such as a glucose sensor, are provided. In vivo conditioning may include modulation of a potential applied to the sensor, such as a glucose sensor implanted or otherwise inserted into the tissue, such as skin, of a subject. The current generated at each potential is used to determine if the sensor is preconditioned and can be relied on to provide a stable signal (see for example FIGS. 3, 6, 7 and 10). In some embodiments, the method is done in vitro for example prior to insertion of the sensor. Such conditioning may be done during or before packaging, or, alternatively, by a user prior to insertion, for example in an appropriate fluid environment. A computing device may be endowed with one or more components of the disclosed apparatuses and/or systems and may be employed to perform one or more methods as disclosed herein.

Disclosed herein is a method for in vivo preconditioning of an indwelling sensor, for example to increase sensor accuracy and to reduce run-in time. In some embodiments, the method is done in vitro, for example prior to insertion of the sensor. Such conditioning may be done during or before packaging, or, alternatively, by a user prior to insertion, for example in an appropriate fluid environment. In various embodiments, the method includes applying a first potential to the sensor and measuring a first current at the first potential. After the first potential is applied, a second potential is applied to the sensor and a second current is measured at the second potential. The relationship, such as the ratio of or differential between, this first current measured to the second current measured is determined. These steps are then repeated cyclically until the relationship, such as the ratio or the differential, between the first current measured and the second current measured has stabilized, thereby reducing sensor run-in time. In some embodiments, the actually currents and the ratio or differential are not measured and/or determined. Instead, the sensor is cycled as described above between the two potentials for a predetermined amount of time.

In embodiments, the first potential is greater than the second potential. While in other embodiments, the second potential is greater than the second. One of ordinary skill in the art can readily understand that whether the first potential is higher than the second or visa-versa depends on the starting potential. What is most important is that there is a difference in the voltage potential applied.

In certain embodiments, the second potential is between about 200 mV and about 900 mV, for example about 200 mV, 225 mV, 250 mV, 275 mV, 300 mV, 325 mV, 350 mV, 375 mV, 400 mV, 425 mV, 450 mV, 475 mV, 500 mV, 525 mV, 550 mV, 575 mV, 600 mV, 625 mV, 650 mV, 675 mV, 700 mV, 725 mV, 750 mV, 775 mV, 800 mV, 825 mV, 850 mV, 875 mV, or about 900 mV. In certain embodiments, the first potential is between about 300 mV and about 1000 mV, for example about 300 mV, 325 mV, 350 mV, 375 mV, 400 mV, 425 mV, 450 mV, 475 mV, 500 mV, 525 mV, 550 mV, 575 mV, 600 mV, 625 mV, 650 mV, 675 mV, 700 mV, 725 mV, 750 mV, 775 mV, 800 mV, 825 mV, 850 mV, 875 mV, 900 mV, 925 mV, 950 mV, 975 mV, or about 1000 mV. In certain embodiments, the potential is varied between 650 mV and 850 mV. When relationship, such as the ratio or the differential, between the current at both of these potentials has stabilized, the modulation is discontinued and the analysis and/or calibration can take place. In embodiments, the first voltage is greater than or equal to the running voltage of the sensor. In embodiments, the second voltage is less than the voltage needed for water hydrolysis. For example with an operation potential of 450 mV conditioning modulation that might occur between 650 mV and 400 mV. Similarly, with an operation potential of 650 mV conditioning modulation that might occur between 850 mV and 650 mV.

It is been found that multiple cycles of variable application of potential results in a more consistent sensor than a single application. Thus in certain embodiments, the cycling is repeated multiple times, such as between about 3 and 20 times. In some embodiments, the cycle is repeated between about 3 and about 10 times. In some embodiments, the first potential is applied for about 5 to about 15 minutes. Generally, since the higher voltage setting is responsible for accelerating the run-in kinetics, the cycle time should be longer at this setting versus the cycle time for the lower voltage, for example 10 min at high voltage. The low voltage setting is used for estimating the completion stage of the run-in process by evaluating the two currents in relation to each other. The lower voltage cycle can therefore be kept relatively short (0.5-5 min), preferably 3-4 min. In certain embodiments, the second potential is applied for about 10 seconds to about 3 minutes. As discussed above, the cycling is repeated until the relationship, such as the ratio or the differential, between the currents at the two applied potentials is substantially consistent. In some embodiments, the cycle is repeated for between about 5 minutes and about 120 minutes, and/or for example, until the relationship (for example the ratio or differential) of the currents at each applied potential is stable.

There is a large background current (phase I) that exists for the first 3 hours once a working potential is applied to a sensor. Typically in a non-conditioned sensor this back ground current would start at between about 8 to 9 nA and would drop rapidly to about 3 nA in the first 3 hours. In addition, in a non-conditioned sensor a second stabilization (Phase II) occurs from 5 nA to 10 nA at the applied potential over the subsequent 12 hours. The method disclosed herein reduces the phase I background current in about 60 minutes and at the same time reduces the phase II background current as well. In certain embodiments, the phase I effect is reduced from greater than 3 hours to less than 60 minutes. In certain embodiments, the phase II effect is reduced about 12 hours to about 60 to about 90 minutes. In some embodiments, the run-in time is reduced from about 8 to about 12 hours to between about 30 minutes and about 60 minutes, such as between about 30 minutes and about 60 minutes after insertion of a sensor into the tissue of a subject, such as a human or veterinary subject. Because not all sensors are identical, the modulation time may be different for each inserted sensor.

In certain embodiments, the method is initiated a few moments after the sensor has been inserted into the tissue, such as the skin or subcutaneous tissue of a subject. Typically, preconditioning can be started after insertion of the sensor into the tissue of a subject, such as within 1 minute, within 2 minutes, within 3 minutes, within 4 minutes, within 5 minutes, within 6 minutes, within 7 minutes, within 8 minutes, within 9 minutes, within 10 minutes, within 11 minutes, within 12 minutes, within 13 minutes, within 14 minutes, or within 15 minutes of insertion. In certain embodiments, the method is initiated after insertion. For example, in some situations the preconditioning method disclosed herein can be performed after the sensor has been implanted for a substantial amount of time to test if the sensor is in good working condition, or perhaps needs to be replaced. Optionally the methods disclosed herein can be performed, for example recycled, to correct or recondition a sensor that is suffering from a non-glucose drift, for example to correct a sensor that is not functioning properly. For example, in embodiments, the method can be preformed after a predetermined time period to determine if the sensor is functioning properly, for example hourly, weekly, or monthly, or at any other predetermined interval after insertion or as triggered by detection of signal drift that is not believed to be due to actual glucose levels. If, during this "reconditioning" the sensor is found to be behaving as it should, for example the relationship, such as the ratio or the differential, of the current from the first applied potential to the current from the second applied current is stable, then the sensor may be left in place. However, if a determination is made that the sensor is not behaving properly, the wearer of the sensor may be prompted to change the sensor. In certain embodiments, the method is performed in response to a determination that the sensor (whether correct or not) is unstable, for example giving unexpected readings. In certain embodiments, preconditioning is performed prior to calibration of the sensor. In embodiments, such as during "reconditioning," the method is performed prior to calibration of the sensor. In some embodiments, the sensor comes from the factory or vendor calibrated and no additional calibration beyond preconditioning is needed. In certain embodiments, the measured current at the first potential and the second potential is between about 1 nA and about 50 nA. In certain embodiments, the ratio between the first measured current and the second measured current is between about 0.5 and about 40. While the method disclosed herein is particularly suited to the preconditioning of glucose sensors in vivo, the method can also be used to condition sensors for other analytes, such as $O_2$, and ionic species, creatinine, urea, among others.

In certain embodiments, the preconditioning is done in vivo. In certain embodiments, the preconditioning is done in vitro. In certain embodiments, the preconditioning is done in vitro. In certain embodiments, the preconditioning is done in a dual phase, for example conditioning can be done in vitro followed by insertion and continued conditioning in vivo.

Reference will now be made to specific examples using the methods described above. It is to be understood that the examples are provided to more completely describe preferred embodiments, and that no limitation to the scope of the invention is thereby intended.

Example

An untreated electrochemical glucose sensor was evaluated for its "normal" settling time according to the following procedure. In this example, the settling time of-the sensor was measured in vitro.

A pig of approximately 40 Kg was placed under an inhaled anesthetic for a period of 6 to 7 hours. A total of 8 Waveform continuous glucose sensors are applied to the skin in the abdominal area of the pig. The sensors are applied using an applicator called a Sensor Insertion Tool. Each sensor in held in place in the skin using an acrylic adhesive patch. The sensor is operated by a devices called a transmitter that contains a potentiostat that is programmed to provide different potentials to the sensors. These potentials can vary from about 400 to about 900 mVolts. Typically, the sensors are platinum based sensors that are coated with a GOx crosslinked glutaraldehyde enzyme layer on top of which is coated a polyurethane outer membrane. Glucose that is located in the interstitial fluid of the skin is analyzed by these sensors. The optimal potential for analysis of glucose is about 650 mV. The current that is generated is composed of two components. One is not related to the glucose concertation and is called the background current and the second is current generated that is directly related to the glucose concertation in the interstitial fluid of the skin.

Figure 3:
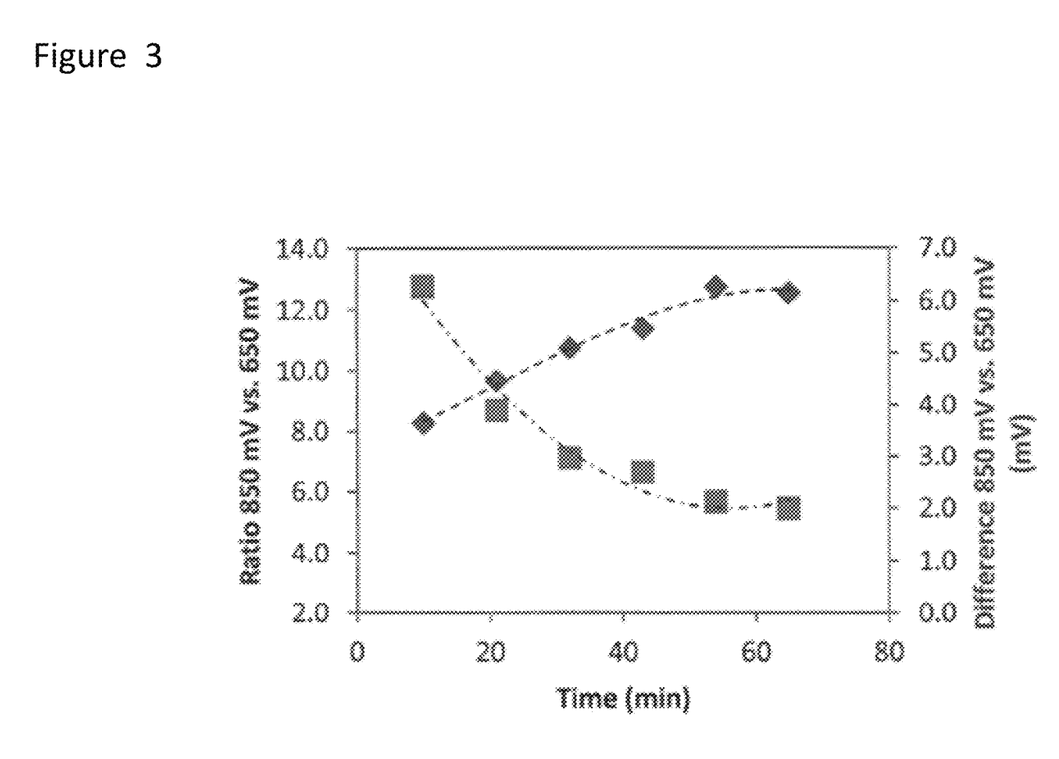
FIG. 3 is a graph showing the ratio of currents at 850 mV and 650 mV over time and the difference in current at 850 mV and 650 mV over time, in accordance with various aspects described herein.
Figure 4:
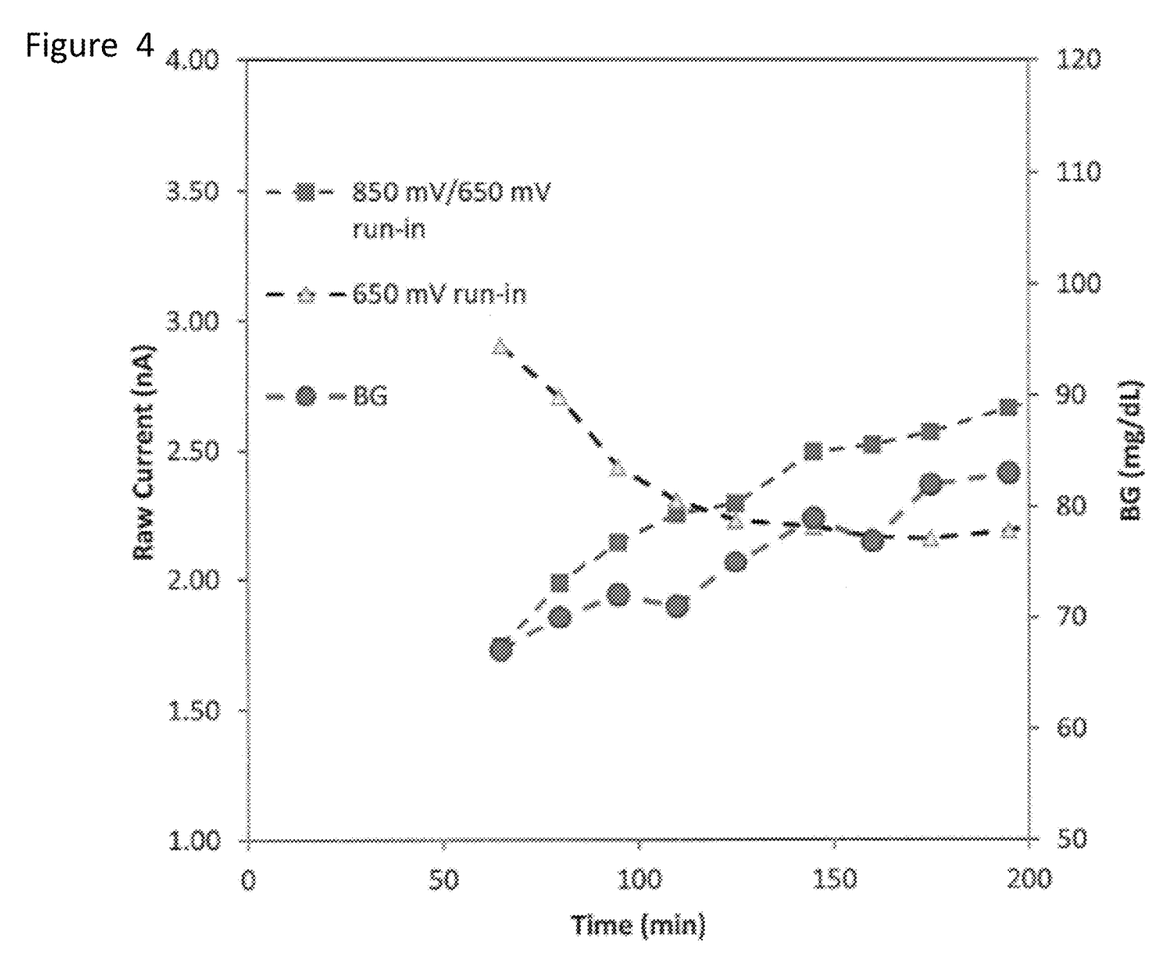
FIG. 4 is a graph of current over time for a sensor with a 650 mV conditioning (run-in), 850 mV/650 mV conditioning (run-in), overlaid with measured blood glucose levels, in accordance with various aspects described herein.
Figure 5:
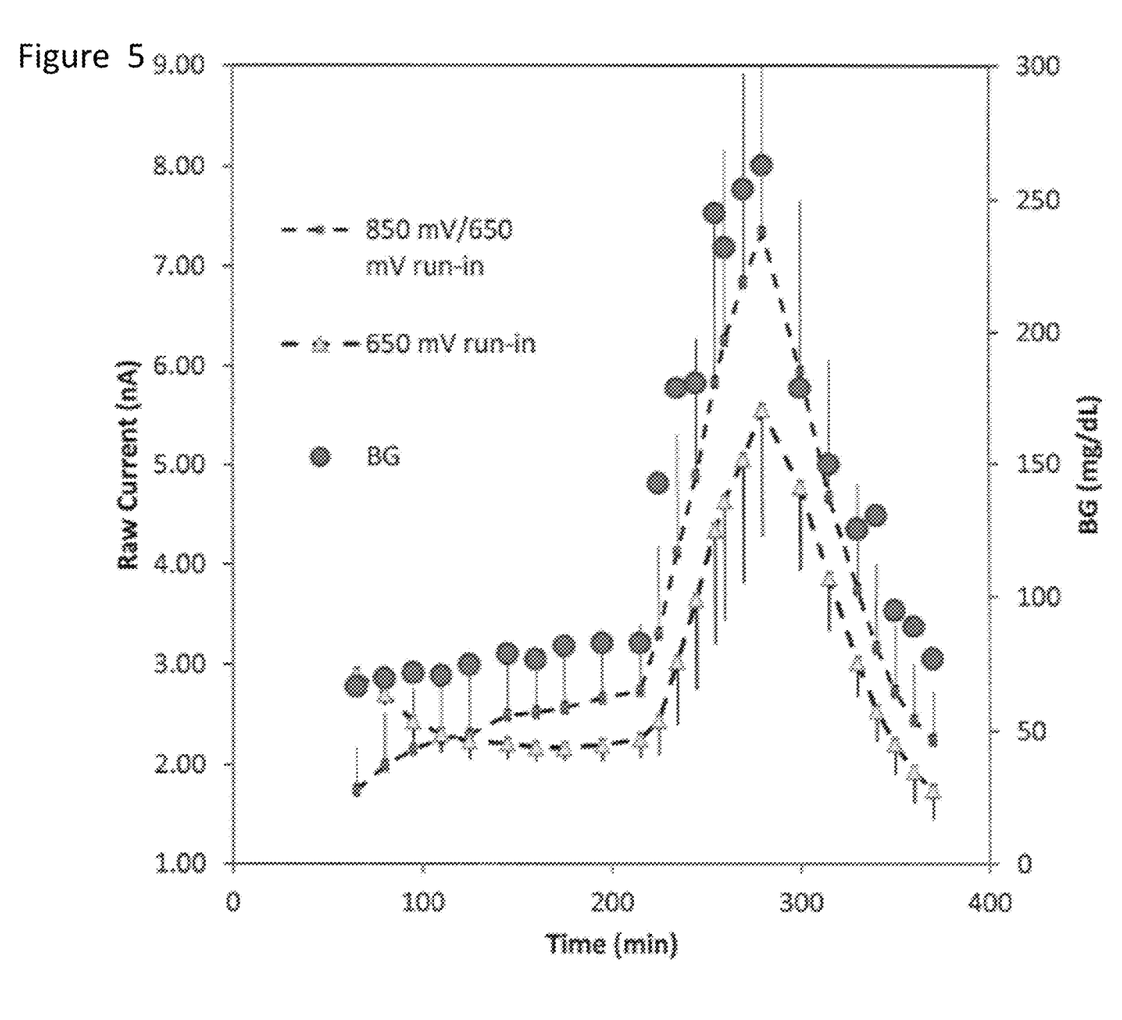
FIG. 5 is a graph of current over time for a sensor with a 650 mV conditioning (run-in), 850 mV/650 mV conditioning (run-in), overlaid with measured blood glucose levels at a later time point and following administration of a glucose bolus, in accordance with various aspects described herein.
Figure 6:
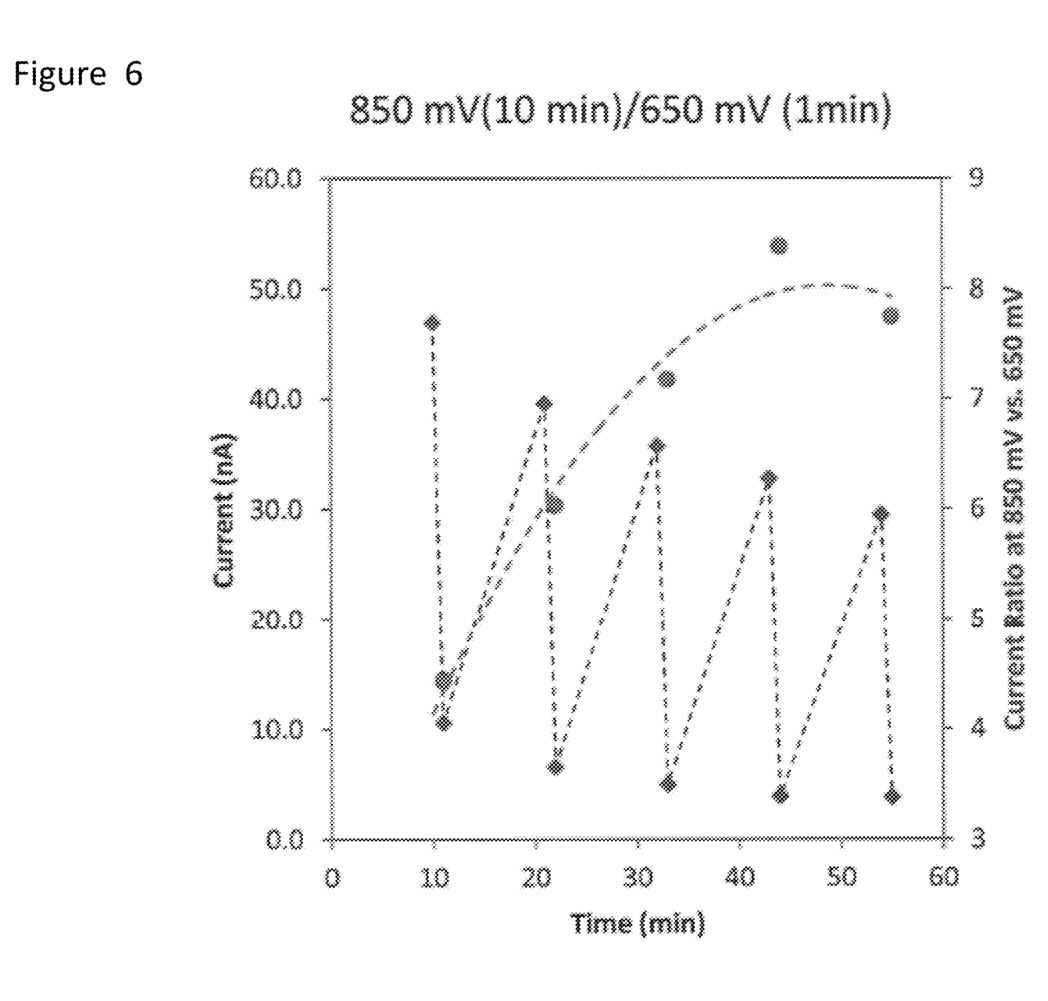
FIG. 6 is a graph of the measured current and the ratio of current for a sensor cyclically preconditioned at 850 mV and 650 mV demonstrating ratio stabilization, in accordance with various aspects described herein.
Figure 7:
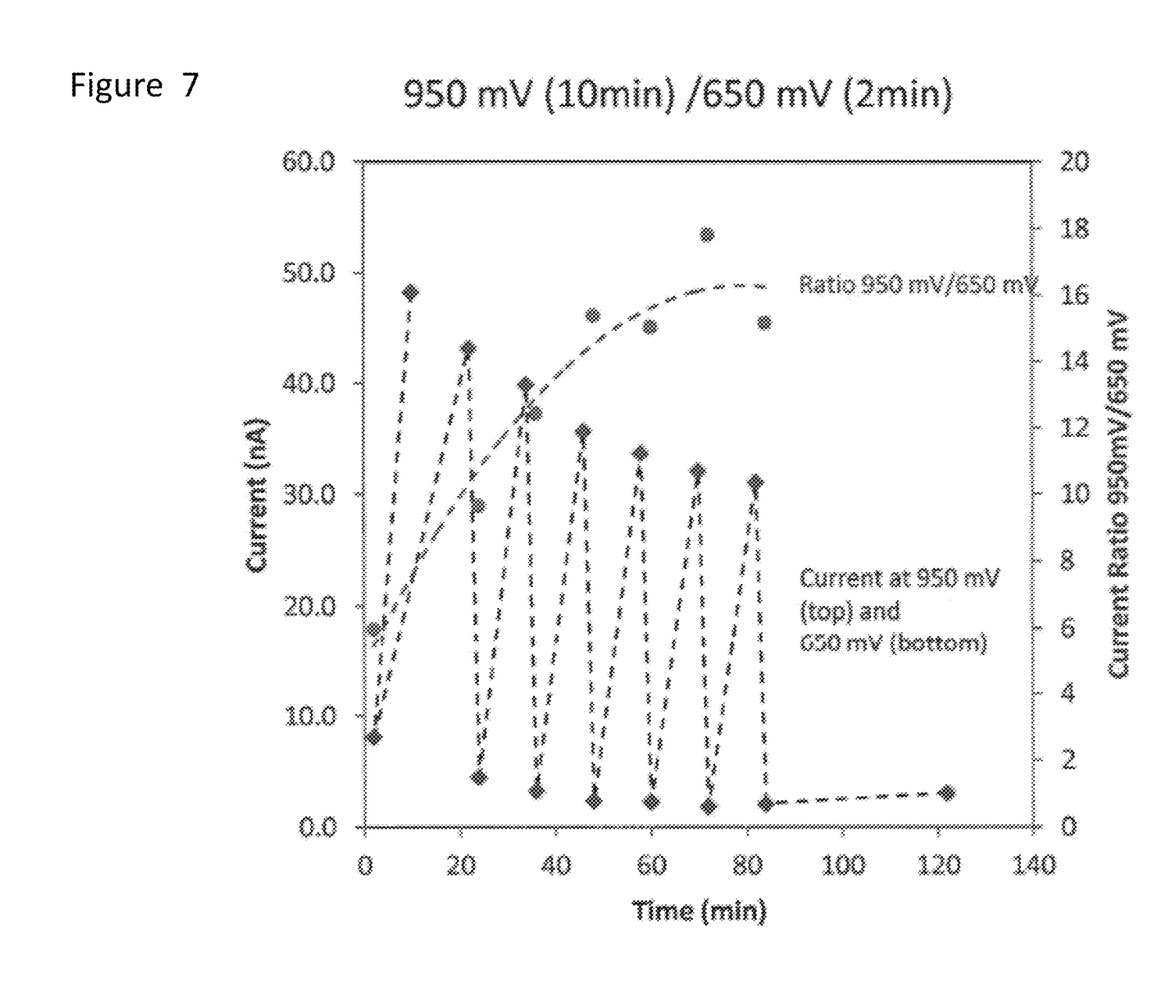
FIG. 7 is a graph of the measured current and the ratio of current for a sensor cyclically preconditioned at 950 mV and 650 mV demonstrating ratio stabilization, in accordance with various aspects described herein.
Figure 8:
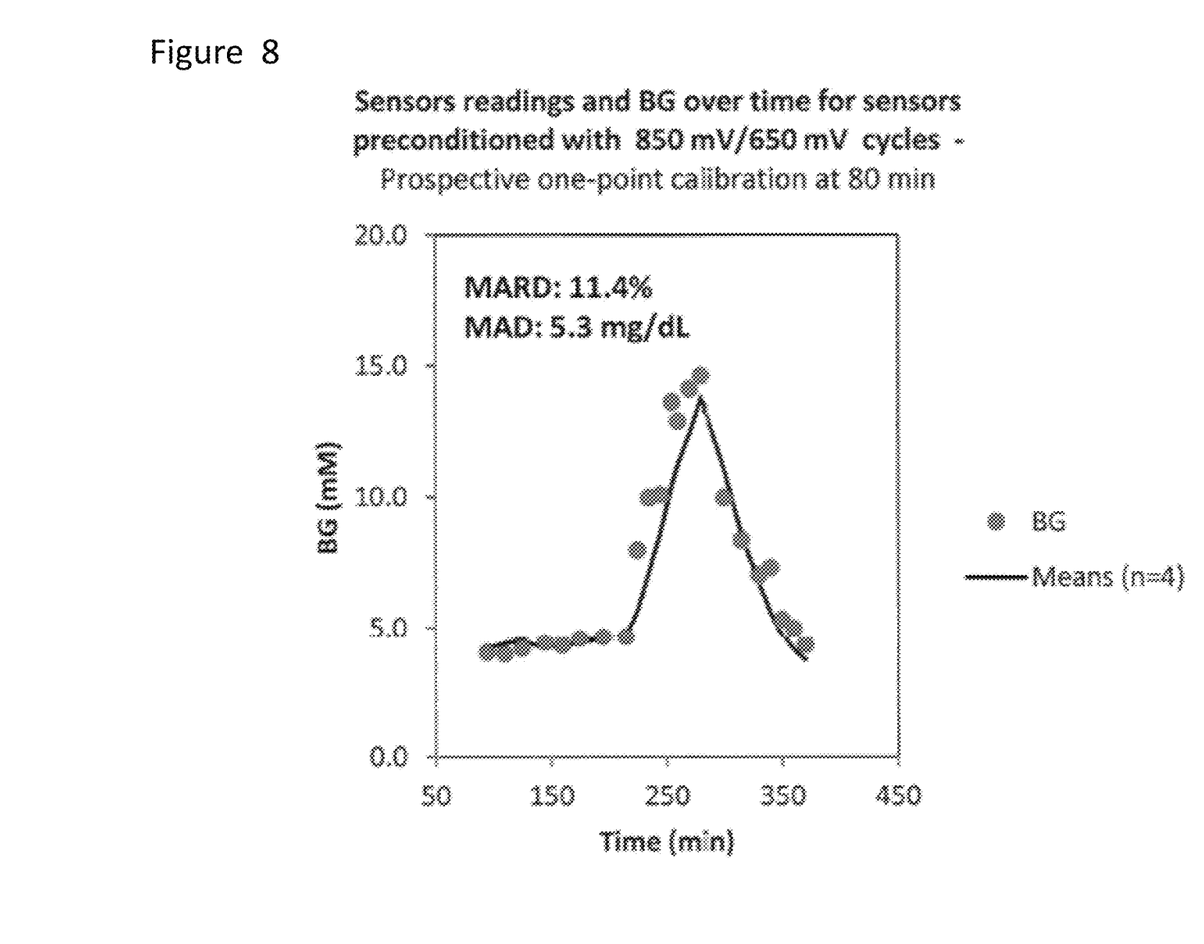
FIG. 8 is a graph illustrating that sensors cyclically preconditioned at 850 mV and 650 mV accurately track blood glucose measurements, in accordance with various aspects described herein.
Figure 9:
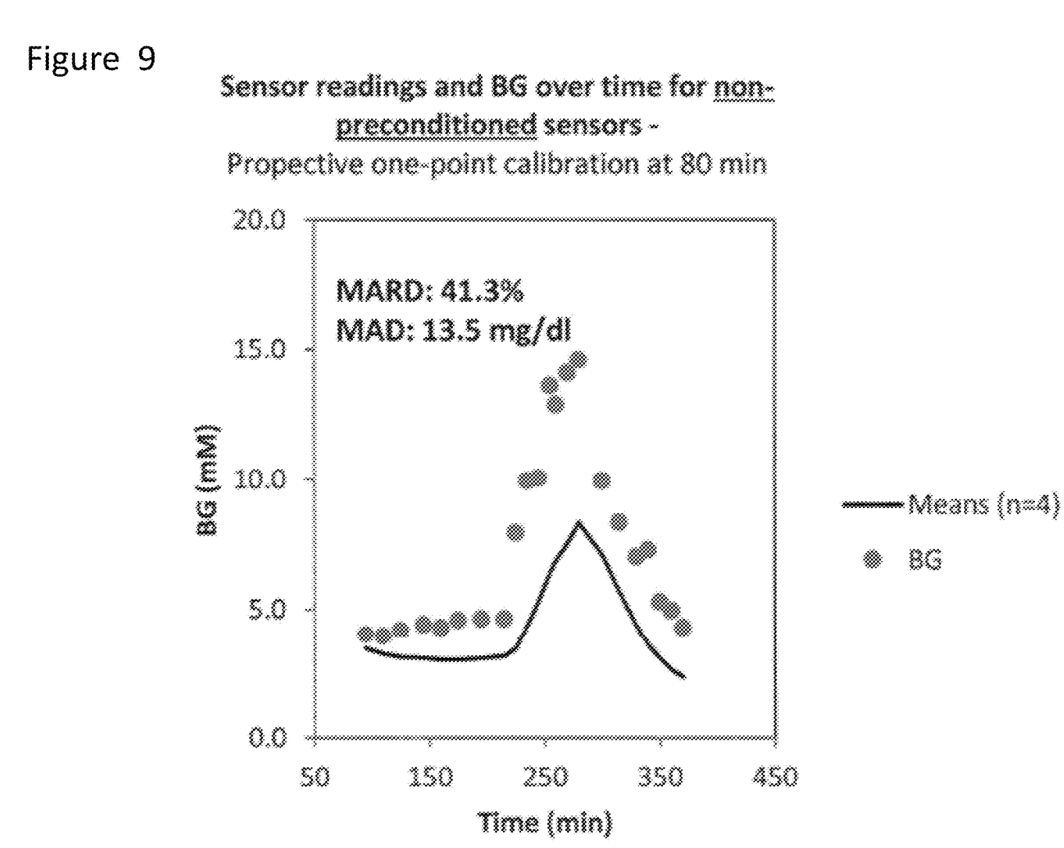
FIG. 9 is a graph illustrating that sensors that are not preconditioned do not accurately track blood glucose measurements, in accordance with various aspects described herein.
Figure 10:
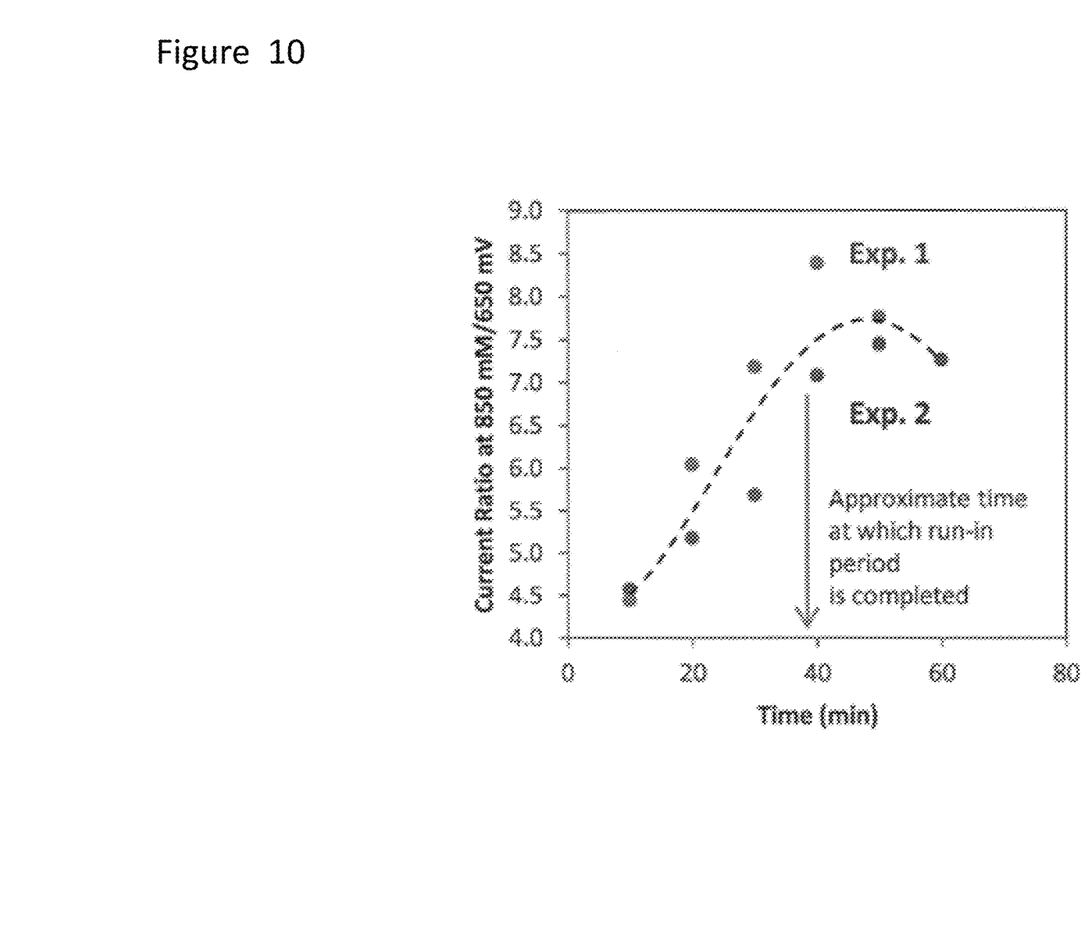
FIG. 10 is graph illustrating that the run-in time (ratio convergence) for two sensors is less than about 40 minutes, in accordance with various aspects described herein.
Figure 11:
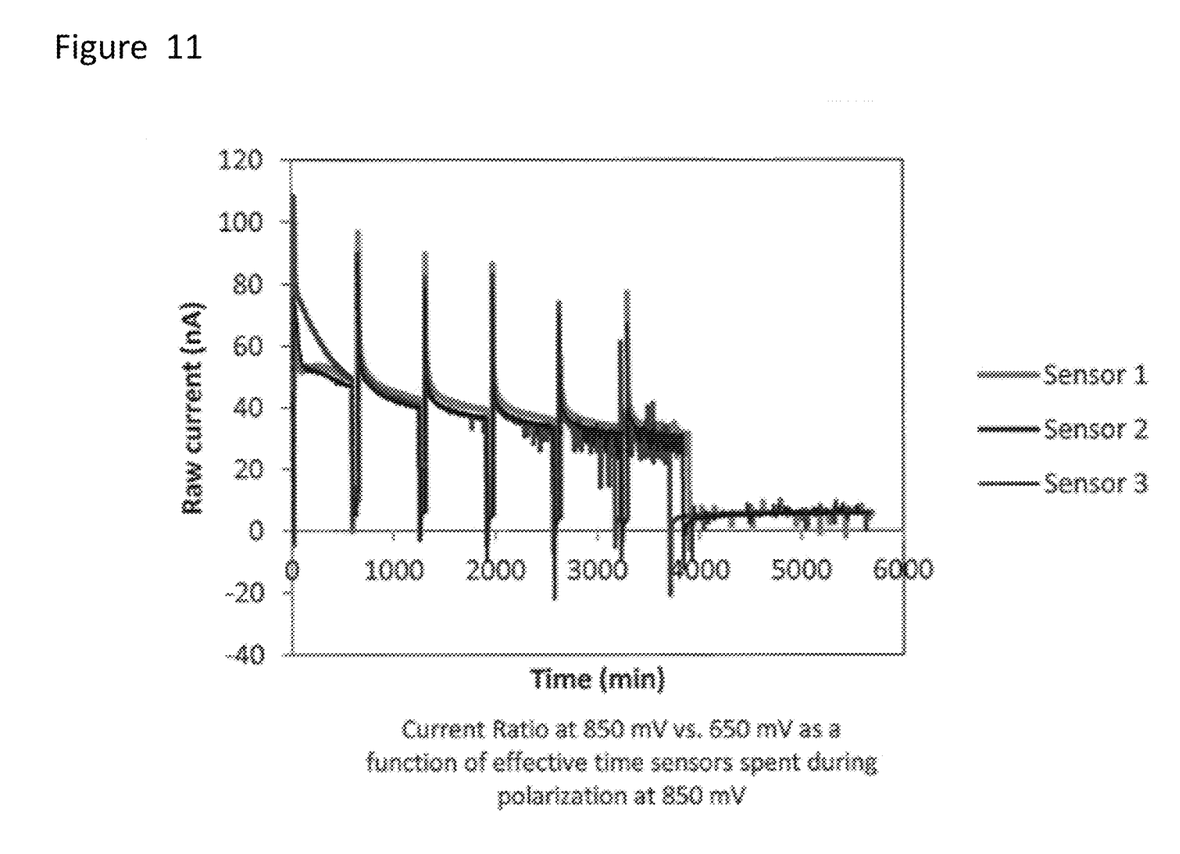
FIG. 11 is a graph showing that raw current is a function of time as the sensors are cycled between 850 mV and 650 mV, in accordance with various aspects described herein.
Figure 12:
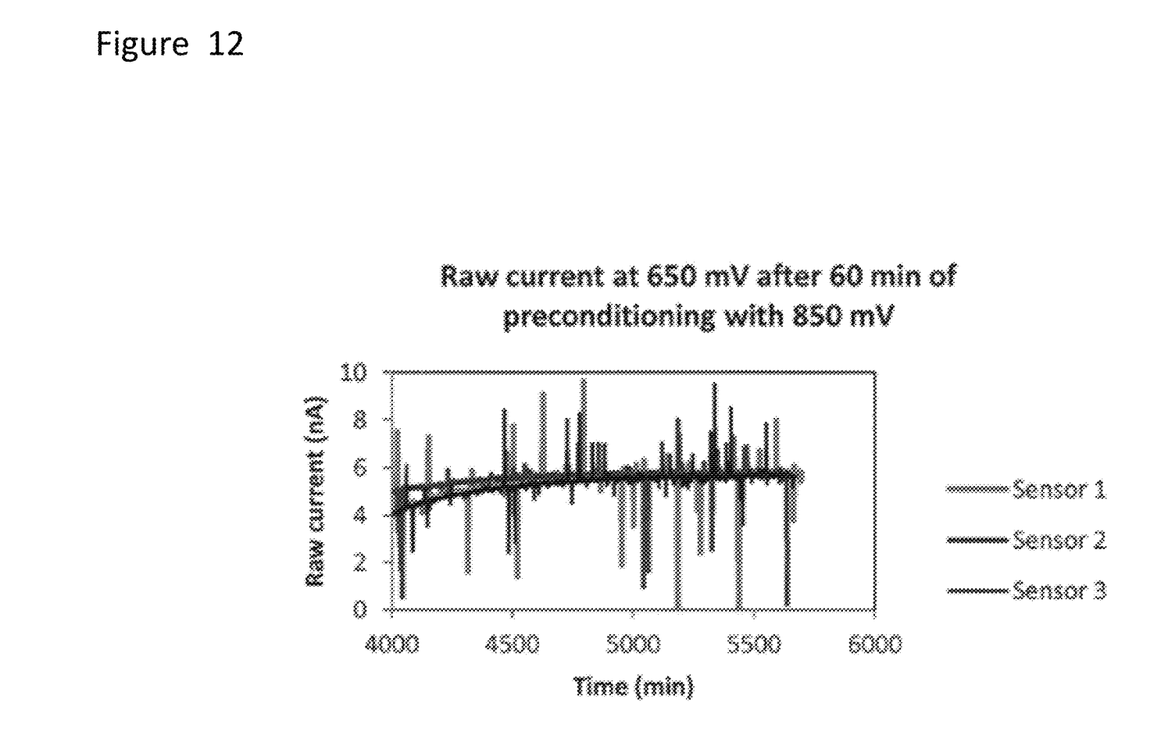
FIG. 12 is a graph showing that raw current is a function of time for sensors preconditioned with 850 mV, in accordance with various aspects described herein.

In the studies depicted in the figures, the transmitters were programed to go through a set of cycles and at a point in time, typically after 60 minutes, the potential is changed to 650 or some other potential and the glucose analysis is carried out. The initial analysis was conducted with the glucose maintained between 60 and 80 mg/dl in concertation. After the initial analysis a 20% glucose solution was infused into a vein of the pig and the glucose concentration was increased to between about 220-270 mg/dl. This higher blood glucose concentration was maintained for about 60 minutes. The blood glucose was then reduced by reducing the amount of glucose that was being infused. The blood glucose levels were checked by using a blood glucose meter and glucose strips. The ear of the pig was punctured and the capillary blood from the ear was obtained and applied to the blood glucose strips to determine the glucose level. The lower level blood glucose level was used to calibrate the ISF based continuous glucose sensors readings. This calibration process involves the conversion of glucose related current generated at the surface to blood glucose equivalent readings. After the conditioning is disclosed herein was done on a number of the sensors their performance was compared to unconditioned sensors. The comparison is made based on the plots shown as well as the MARD (Mean Absolute Relative Differences) calculations. The MARD calculations were made by comparing CGM glucose values to blood glucose concentrations collected at the same time. It was clear for both the graphing and the MARD analysis that conditioned sensors performed much better than those that were not conditioned. FIG. 1 is a graph showing the average current from four sensors with an applied potential of 650 mV. FIG. 2 is a graph showing the average current from four sensors that were preconditioned with cycles of applied potentials of 850 mV and 650 mV. FIG. 3 is a graph showing the ratio of currents at 850 mV and 650 mV over time and the difference in current at 850 mV and 650 mV over time. FIG. 4 is a graph of current over time for a sensor with a 650 mV conditioning (run-in), 850 mV/650 mV conditioning (run-in), overlaid with measured blood glucose levels. FIG. 5 is a graph of current over time for a sensor with a 650 mV conditioning (run-in), 850 mV/650 mV conditioning (run-in), overlaid with measured blood glucose levels. FIG. 6 is a graph of the measured current and the ratio of current for a sensor cyclically preconditioned at 850 mV and 650 mV demonstrating ratio stabilization. FIG. 7 is a graph of the measured current and the ratio of current for a sensor cyclically preconditioned at 950 mV and 650 mV demonstrating ratio stabilization. FIG. 8 is a graph illustrating that sensors cyclically preconditioned at 850 mV and 650 mV accurately track blood glucose measurements. FIG. 9 is a graph illustrating that sensors that are not preconditioned do not accurately track blood glucose measurements. FIG. 10 is graph illustrating that the run-in time (ratio convergence) for two sensors is less than about 40 minutes. FIG. 11 is a graph showing that raw current is a function of time as the sensors are cycled between 850 mV and 650 mV. FIG. 12 is a graph showing that raw current is a function of time for sensors preconditioned with 850 mV.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

The invention claimed is:

1. A method of conditioning of an indwelling sensor to reduce run-in time, comprising:
performing a plurality of conditioning cycles, wherein each conditioning cycle is performed by:
measuring a current of the indwelling sensor when applying a first potential to the indwelling sensor in a respective time period, wherein the first potential is greater than or equal to a running voltage of the indwelling sensor,
measuring the current of the indwelling sensor when applying a second potential to the indwelling sensor in a respective time period, wherein the first potential is greater than the second potential and the respective time period in which the first potential is applied to the indwelling sensor is greater than the respective time period in which the second potential is applied to the indwelling sensor, and
determining a ratio of the current measured when applying the first potential to the current measured when applying the second potential; and terminating the conditioning cycles when the ratio has stabilized.

2. The method of claim 1, where the second potential is between about 200 mV and about 900 mV and the first potential is between about 300 mV and about 1000 mV.

3. The method of claim 1, where the second potential is between about 200 mV and about 900 mV and the first potential is between about 700 mV and about 900 mV.

4. The method of claim 1, where at least 3 of the conditioning cycles are performed.

5. The method of claim 1, where in each conditioning cycle, the first potential is applied for about 30 seconds to about 15 minutes and the second potential is applied for about 10 seconds to about 3 minutes.

6. The method of claim 1, where the method is repeated for between about 5 minutes and about 120 minutes.

7. The method of claim 1, where the indwelling sensor comprises a glucose sensor.

8. The method of claim 1, where the method is initiated before about 5 minutes after insertion of the indwelling sensor into a tissue of a subject.

9. The method of claim 1, where the method is performed after a predetermined time period to determine if the indwelling sensor is functioning properly.

10. The method of claim 1, where the method is performed in response to a determination that a signal drift as recorded by the indwelling sensor does not correspond to actual levels of an analyte the indwelling sensor is configured to measure.

11. The method of claim 1, where the measured current when applying the first potential and when applying the second potential is between about 1 nA and about 50 nA.

12. The method of claim 1, where in each conditioning cycle the ratio is between about 3 and about 14.

13. The method of claim 1, where the method is performed prior to calibration of the indwelling sensor.

14. The method of claim 1, where the method is performed in vitro prior to insertion of the indwelling sensor into a tissue of a subject.

15. The method of claim 1, where the method is performed partially in vitro prior to insertion of the indwelling sensor into a tissue of a subject and partially in vivo after insertion of the indwelling sensor into the tissue of the subject.

16. The method of claim 1, wherein in each conditioning cycle the respective time period in which the first potential is applied to the indwelling sensor is 10 minutes or more and the respective time period in which the second potential is applied to the indwelling sensor is 5 minutes or less.

17. The method of claim 1, wherein in each conditioning cycle the respective time period in which the first potential is applied to the indwelling sensor is at least twice the respective time period in which the second potential is applied to the indwelling sensor.

18. The method of claim 1, wherein in each conditioning cycle the respective time period in which the first potential is applied to the indwelling sensor is at least ten times the respective time period in which the second potential is applied to the indwelling sensor.

19. The method of claim 1, wherein in each conditioning cycle the respective time period in which the first potential is applied to the indwelling sensor is at least five times the respective time period in which the second potential is applied to the indwelling sensor.

20. The method of claim 1, wherein the second potential is used for estimating a completion of the run-in of the indwelling sensor.

21. The method of claim 1, wherein in each conditioning cycle the respective time period in which the first potential is applied to the indwelling sensor is at least twenty times the respective time period in which the second potential is applied to the indwelling sensor.

* * * * *